United States Patent [19]
West

[11] Patent Number: 4,737,650
[45] Date of Patent: Apr. 12, 1988

[54] INSPECTION APPARATUS
[75] Inventor: Robert N. West, Chislehurst, England
[73] Assignee: Sira Limited, Kent, England
[21] Appl. No.: 38,487
[22] Filed: Apr. 13, 1987

Related U.S. Application Data
[63] Continuation of Ser. No. 779,753, Sep. 24, 1985, abandoned.

[30] Foreign Application Priority Data
Sep. 24, 1984 [GB] United Kingdom ............... 8424084
[51] Int. Cl.$^4$ ............................................. G01N 21/88
[52] U.S. Cl. ................................... 250/571; 356/237
[58] Field of Search ............... 250/571; 356/243, 431, 356/237, 446, 445

[56] References Cited
U.S. PATENT DOCUMENTS
4,522,497 6/1985 Ikin ........................................ 250/571
4,629,319 12/1986 Clarke et al. ........................ 356/446

Primary Examiner—Gene Wan
Attorney, Agent, or Firm—Sughrue, Mion, Zinn, Macpeak & Seas

[57] ABSTRACT

A beam of radiation is scanned across a sheet 13 and is either reflected therefrom or transmitted therethrough. Faults in the sheet 13 deflect, scatter or alternate the beam which is then passed to a retroreflector screen 24 where it forms an image 15. Analysis of the image 15 is carried out via the scanning means 22 to determine the faults in the sheet 13.

11 Claims, 3 Drawing Sheets

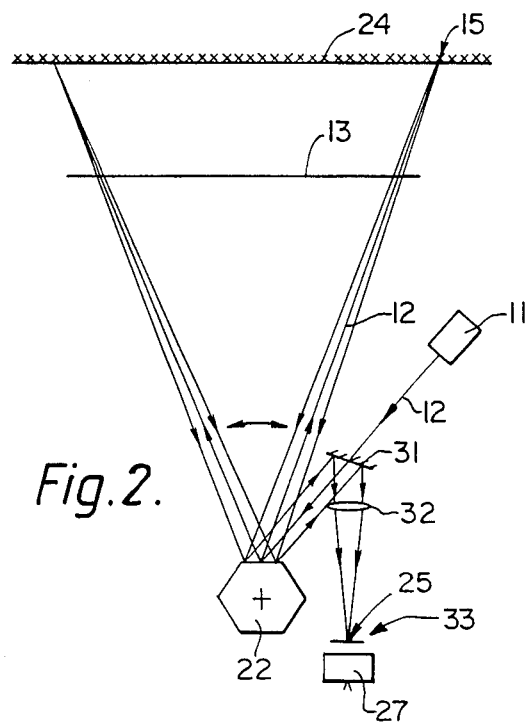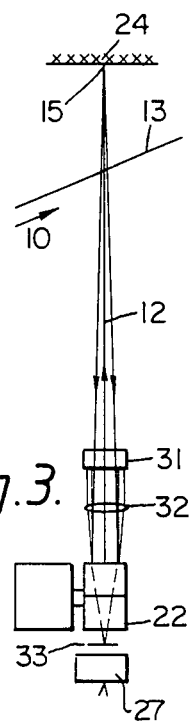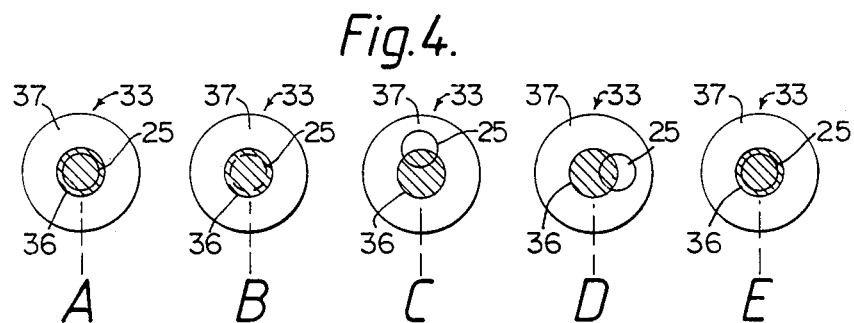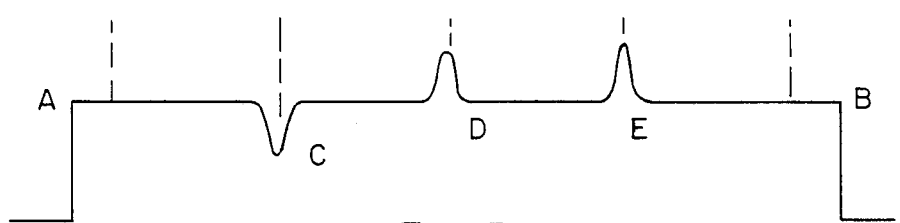

INSPECTION APPARATUS

This application is a continuation of application Ser. No. 779,753 filed Sept. 24, 1985, now abandoned.

The present invention relates to inspection apparatus.

BACKGROUND OF THE INVENTION

The apparatus may be of a type for inspecting an object for example for inspecting its surface or, if the object is transparent to the radiation used in the inspection, for inspecting the bulk of the object. Preferred arrangements of the apparatus are particularly applicable to the inspection of sheet material.

Our previous patent No. 2 054 835 disclosed an inspection apparatus in which two beams of light which have been influenced by different portions of an object were passed to a grating 14, the two beams being spaced at the grating by an uneven number of widths "w" which correspond to the widths of the alternate light and dark areas of the grating. Light collected from the grating would be of a constant amplitude so long as the two beams are spaced apart by that exact distance, but faults or flaws in the object under test would cause the distance between the two beams to change and therefore cause a difference in the light received from the grating. This could be used to indicate a fault or flaw in the object or suface under test.

Although such a system operates satisfactorily there are a number of difficulties. Where a sheet material is to be inspected which is of considerable width, then a grating 14 of the same width as the sheet material must be provided. This increases the cost and complexity of the apparatus. Furthermore a cylindrical lens 26 is utilised and once again the cylindrical lens is an expensive component and the length must be sufficient so as to enable the whole of the width of the sheet material to be scanned.

Furthermore, the arrangement only deals with deflections of the beam in one plane so that deflections in the plane of FIG. 3 are detected, but deflections at right angles to the plane of FIG. 3 would not be detected and certain defects would therefore not be detected.

Another inspection apparatus is described in U.S. Pat. No. 3,790,287. Somewhat similar problems arise with this arrangement. There is described an apparatus for examining a silicon wafer which of course is of limited size. Thus the scanned beam passing to the wafer 28 passes through a lens system 26 which must clearly be of sufficient lateral extent so as to be able to receive the beam at the extremes of its scanning path. Clearly such an arrangement is limited to examination of quite small objects and would not be suitable for large sheets.

Furthermore, the arrangement only looks at faults on the surface of the wafer because an image of the surface itself is formed at the detector 38 (this is not totally clear but would seem likely from the ray diagram in FIG. 1) and so the arrangement is not suitable for examining, for example, transparent objects in which the beam passes through the object.

SUMMARY OF THE INVENTION

The present invention has been based on the realisation that if a beam of light is passed to the object and is either reflected therefrom or transmitted therethrough, faults in the object will cause changes in the beam, for example, deflection of the beam, scattering of the beam or attenuation of the beam. If the affected beam is then passed to, for example, a screen, we can examine the image of the beam and from that image of the beam we can analyse the faults in the object. This is rendered simpler if we are able to examine this image through the scanning system so as to "descan" the image.

The present invention provides inspection apparatus for inspecting an object comprising means for scanning a beam of radiation across an object under test, means for receiving the beam of radiation and forming an image thereon after the beam has been influenced (e.g. by refraction, reflection, transmission) by said object, means for examining the image formed by the beam on the receiving means comprising focusing means for forming a focused image of said image on a detector means via the scanning means, the detector means being sensitive to changes in the position and/or intensity of the image formed thereon caused by the influence of the object.

It should be understood that although faults or flaws in the object are referred to there may be certain circumstances in which the particular fault or flaw may comprise a deliberately produced feature of the object under test. The term "radiation" may be taken to be radiation of any wavelength but particularly optical light or ultra violet or infra red radiation.

Various apparatus of the invention may be produced to inspect a variety of objects which influence the beam of radiation, for example the surface of sheet material which reflects at least a proportion of the incident beam or the body of sheet material which transmits the beam. Thus the apparatus may be used to inspect, for example, sheet material such as tin plate, plastic film, glass or the like.

Preferably the means for receiving the beam of radiation comprises a scattering screen, which may be for exaple, paper or ground glass. Alternatively the screen may comprise a retro-reflective screen. An advantage of this arrangement is that most of the light from the beam striking the retro-reflective screen will be reflected back automatically to the scanning system.

The detector means preferably includes an analyser means for analysing the focused image. The detector means may include two areas, one of which influences the focused image in a different way to the other, the focused image beng passed to one of the areas when the object under test is normal and being deflected to or toward the other area when the focused image is influenced by a fault in the object under test.

In this case one of the two areas may have at least one dimension which generally corresponds to the outer dimesnion of the focused image where it strikes the area so that any deflection of the focused image away from the first area causes the focused image to pass into the second area adjacent the second area. One of the areas is preferably the same shape as the cross section of the focused image and the other of the areas is next to or surrounds the first area.

BRIEF DESCRIPTION OF THE DRAWINGS

Preferred arrangements of the invention will now be described by way of example only and with reference to the accompanying drawings in which:

FIG. 2 shows a front view in a diagrammatic form of the apparatus of the invention, FIG. 3 shows a side view of the apparatus of FIG. 2, FIGS. 4A to 4E show diagrammatically the two areas used in the apparatus and the incidence of the beam on those two areas, FIG. 5 shows a signal output.

DESCRIPTION OF THE PREFERRED EMBODIMENT

Figure 1:
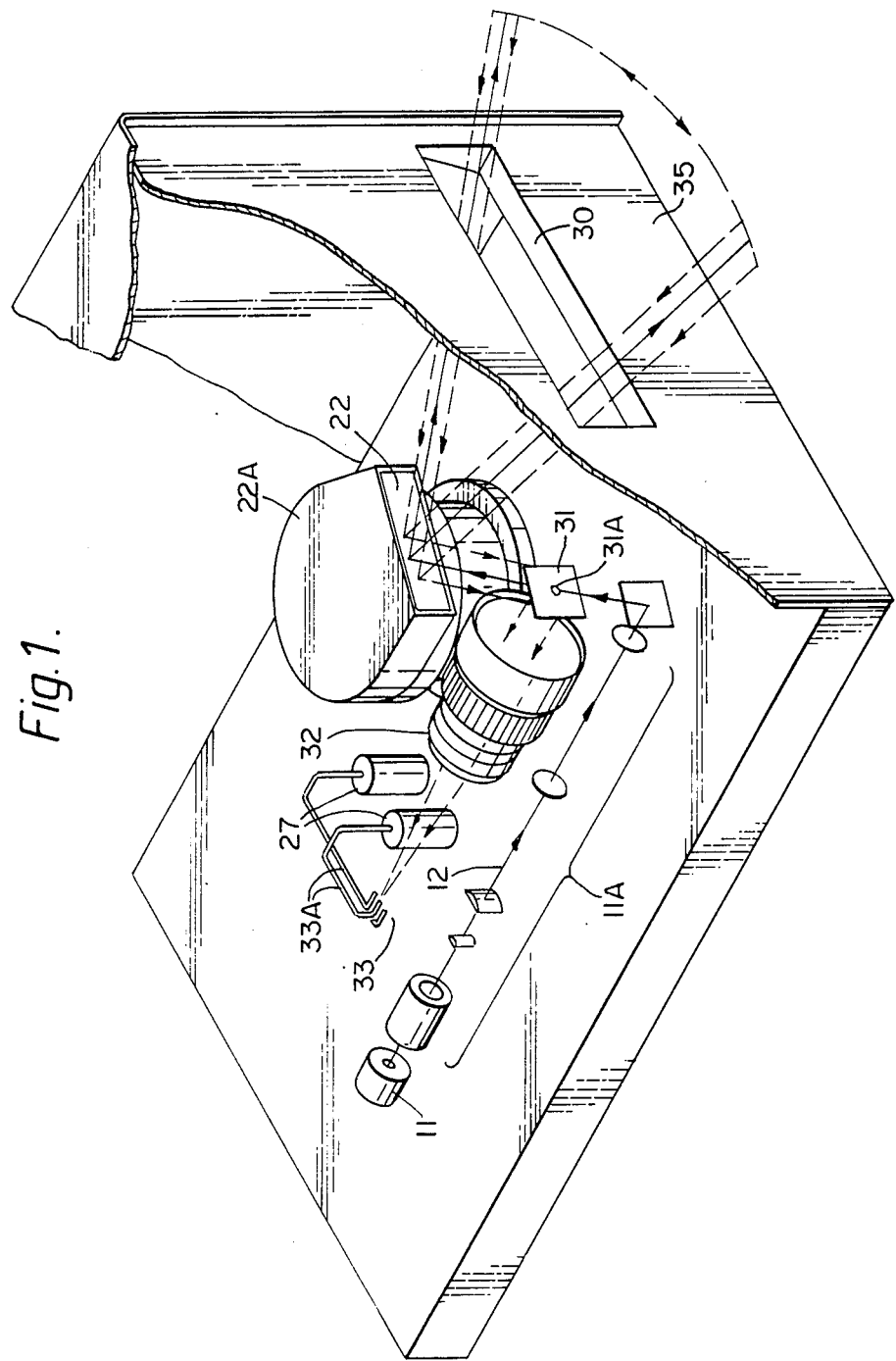
FIG. 1 is a perspective broken away isometric view of a part of a preferred inspection apparatus according to the invention.

Referring to FIGS. 1, 2 and 3, the apparatus comprises a laser 11 and beam shaping optical components 11A for producing a beam 12. The beam 12 passes through a beam splitter 31 in the form of a mirror having a central aperture 31A through which the beam from the laser 11 passes. The beam is reflected from a mirror drum scanner 22 mounted inside a hood 22A (see FIG. 1) so as to scan the beam 12 through a slot 30 in a box 35 containing the laser and optical components transversely across the object 13 under inspection which in this case may be a sheet of transparent material 13. In this preferred arrangement the sheet of material 13 is moving at right angles to the line of scan as illustrated by the arrows 10 in FIG. 2 whereby the whole of the sheet 13 may be inspected by means of a combination of scanning movement of the beam and movement of the sheet 11. The mirror drum scanner 22 thus causes the light beam 12 to scan from one edge of the sheet 13 to the other as shown in FIG. 1.

Light transmitted by the sheet 13 is passed onto a retro-reflective sheet 24 which extends behind the sheet 13 where an image 15 of the incident beam which is passed through the sheet 13 is formed. In fact the image 15 is not a focused image but is actually simply a cross section of the form of the beam where it strikes the sheet 24.

The slightly scattered retro-reflected beam passes back to the sheet 13, passes through the sheet 13 and onto the mirror drum scanner 22 where the scanning motion is cancelled, to the beam splitter 31 where it is reflected and is collected by collection lens 32. It will be noted that the outward beam from the laser it is very narrow and passes through the aperture 22A of the beam splitter 31 but the returning beam is scattered and is intercepted by all of the mirror surface of the beam splitter 31. It is arranged that the retro-reflective layer 24 and the target apparatus 33 are at conjugate points with respect to the lens 32 so that a focused image 25 of the image 15 is formed by the lens 32 onto a target apparatus 33. Note that, whereas the image 15 is simply the cross section of the beam at the retro-reflective layer 24, the focused image 25 is a genuine focused image of the part of the surface of the retro-reflected layer 14 which the image 15, in normal circumstances, will occupy.

The target apparatus 33 comprises the ends of optical fibres 33A and light passes through these fibres to respective photomultipliers 27.

The beam 12 passing from the mirror drum 22 to the retro-reflective layer 24 has a very small cross section (typically 0.25 to 0.5 mm diameter at the sheet 13). Thus even small defects in the sheet 13 will severely affect the beam. In normal circumstances the beam then passes to the retro-reflector at which point it is about 3 mm in diameter (in the case where the sheet 13 is separated from the retro-reflector 24 by about 1 meter) and the retro-reflector reflects the beam with an angle of scatter of about 1 to 2° so that when the beam reaches the sheet 13 again its diameter is about 30 mm. In practice as the facets of the mirror drum are normally about 2.5×5 cm these define the cone of light which will be received by beam splitter 31 and the lens 32. However, it will be noted that although the small fault in the sheet 13 affects the beam from the mirror drum 22, the returning beam from the retro-reflector 24 is very much larger and thus only a very small part of the reflected beam from the retro-reflector 24 is affected by the same fault. Thus if, for example, the fault in the sheet 13 deflects the beam 12 then the retro-reflector 24 will retro-reflect the beam back to the sheet 13 with a degree of scattering and the majority of the returning beam will not be affected the second time by the defect and will therefore not pass back to the mirror drum 22. It is only that very small proportion of the reflected beam which strikes the same defect which will be scattered back along the incident path to the mirror drum 22 and this small proportion is of no consequence.

It will be understood that as the beam path from the laser to the scanner 22 does not move then the beam path from the scanner 22 to the beam splitter and hence the target 33 similarly does not move when the sheet 13 does not deflect the beam and so the focused image 25 remains stationary on the target 33.

A front view of the target apparatus 33 is shown in FIG. 4. In this case there is provided a first area in the form of a central circle 36 of material which transmits half of the incident beam. The central circle 36 is surrounded by an outer annulus 37 which transmits all of the incident beam. The image 25 of the beam is shown at 12. Referring now to FIG. 4A it will be understood that the outline of the image 25 is equal to or less than the diameter of the central circle 36 and so long as the sheet material does not have any faults or flaws which deflect the beam then the image 25 will remain in the central circle 36. FIG. 5 shows the signal output corresponding to FIGS. 4A to 4E. If the beam passes through an absorbing defect in the sheet 13 then the light received by the photomultiplier 27 will be reduced as is indicated by the signal at C in FIG. 5. If the beam 12 passes through a portion of the sheet 13 which includes a defect which deflects the beam then the image 15 will move away from the portion it would otherwise hold and hence the image 25 will be deflected away from the central circle 36 into the outer annulus 37 and hence the light passing through to the photomultiplier 27 will be increased as is shown at D in FIG. 5. Indeed deflections of the beam in any direction as shown at E in FIG. 11 will produce an increase in the signal produced by the photomultiplier 27.

This latter arrangement therefore has the advantage that deflection of the beam in any direction by the sheet 13 will be readily indicated.

Figure 6:
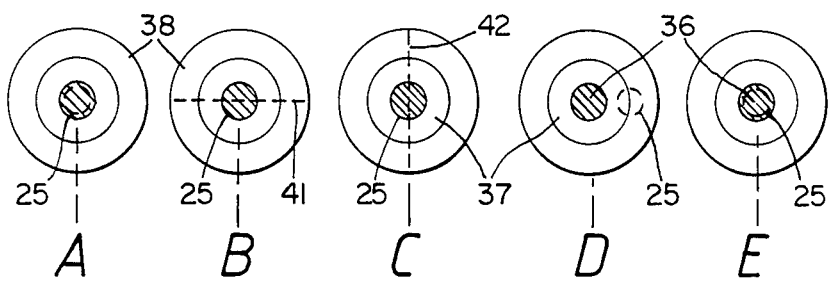
FIGS. 6A to 6E show alternative arrangements of FIGS. 4A to 4E.
Figure 7:
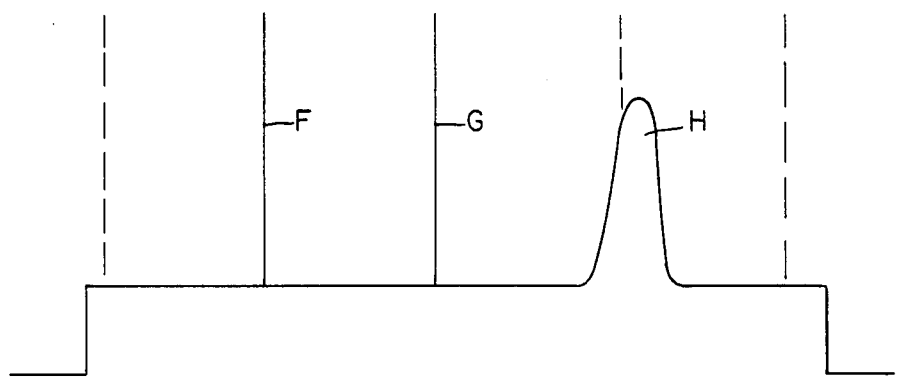
FIG. 7 shows the signal output from the apparatus of FIG. 6, and, FIG. 8 shows an alternative arrangement of target apparatus.

FIGS. 6 and 7 illustrate an alternative arrangement of the target apparatus 33 in which other types of fault in the sheet material 13 can be detected. Thus if a further annulus 38 is provided surrounding the outer annulus 37 and the light in this further annulus 38 is collected separately then an analysis of the light collected in this further annulus 38 will give an indication of the type of flaw or fault in the sheet material 13. For example some faults or flaws in the sheet material 13 such as scratches will scatter the light thus forming a larger image 15 on the retro-reflective layer 14 and this the focused image 25 of this larger image 15 will be picked up by the further annulus 38. The signal output for this further annulus 38 is shown in FIG. 7. At F and G there are shown the effects on the signal output of the further annulus 38 for vertical and horizontal scratches 41,42. Of course if there is a fault in the sheet 13 which severely distorts the beam 12 and hence the images 15 and 25 as is indicated at H (see FIG. 6D and FIG. 7) then this will also be picked up by the further annulus 38.

Advantages of the apparatus are that there is good ambient light rejection because the detector is only looking at a focused image 25 of the position which the image 15 occupies or should occupy, there is a sensitivity to all types of distortion, i.e. distortion causing the image 15 to move along or transverse to the direction of scanning and fine scratches and small inclusions can also be detected by the further annulus 38. The apparatus is almost completely free of the need for accurate registration between the scanning head and the simple retro-reflective screen since the field of view of the collection system is the same as that of the projection system.

An alternative arrangement using fibre optics to segment the target area and using a number of separate detectors to analyse the image.

Figure 8:
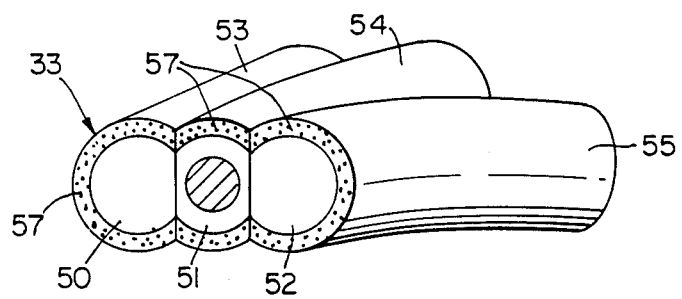

Referring to FIG. 8 the target 33 comprises three separate areas 50, 51, 52 which are provided by the ends of three optical fibres 53, 54, 55 repectively. Area 51 corresponds to both areas 36 and 37 of FIG. 6 and the two areas 50, 52 correspond to the area 38 of FIG. 6. It will be noted that the outer coating 57 of the three optical fibres 53, 54, 55 are cut away where the three fibres 53, 54, 55 abut so as to form a continuous surface.

Optical fibres 53 and 55 are joined together and passed to one detector and optical fibre 34 passes to a second photodetector.

Various other forms of target filter could also be used such as a circularly graded neutral density area with the darkest area in the centre so that the distortion aspect could be further classified in intensity.

This invention is not restricted to the details of the foregoing examples.

Although we have described the apparatus with repsect to a retro-reflecting surface 24 the arrangement would operate with a simple scattering screen such as a paper surface or a ground glass screen. However the retro-reflecting layer 24 allows the collection of a greater proportion of the incident light.

Furthermore the appratus of the invention has been described with regard to the inspection of a transparent sheet 13. Reflective material may also be inspected in which case the beam reflected from the surface would be passed to a retro-reflector 24 and thence back to be reflected again by the surface before being collected by the mirror drum 22.

I claim:
1. Inspection apparatus for inspecting an object, comprising:
    means for forming a narrow beam of radiation for transmission along a first optical path;
    a rotatable mirror drum comprising a plurality of facets, said mirror drum being disposed in said first optical path for scanning said beam of radiation across an object under test that is located across said first optical path and is radiation transmissive;
    reflective screen means in said first optical path for receiving the beam of radiation after the beam has been transmitted by said object, said beam forming an image on said reflective screen means, said reflective screen means reflecting said image along a second optical path back toward said object and said rotatable mirror drum;
    focusing means located on said second optical path for bringing said image into focus after further transmission of said reflected image by said object;
    a detector means located on said second optical path for receiving said focused image, the detector means being sensitive to changes in (a) the position in any direction; (b) the size, and (c) the intensity of the image formed thereon caused by the influence of the object;
    the detector means and the reflective screen being at conjugate points with respect to the focusing means; and
    means for analyzing the focused image and thereby inspect the object.

2. Apparatus as claimed in claim 1 in which the reflection screen means for receiving the beam of radiation comprises a radiation scattering screen.

3. Apparatus as claimed in claim 2 in which the reflection screen means for receiving the beam of radiation comprises a retro-reflective screen.

4. Apparatus as claimed in claim 3 in which said detector means includes two areas, one of which influences the focused image in a different way to the other, the focused image being passed to one of the areas when the object under test is normal and being deflected to or toward the other area when the focused image is influenced by faults in the object under test.

5. Apparatus as claimed in claim 4 in which one of the two areas has at least one dimension which generally corresponds to the outer dimension of the focused image where it strikes the area so that any deflection of the focused image away from that first area causes the focused image to pass into the second area.

6. Apparatus as claimed in claim 5 in which one of the areas is the same shape as the cross section of the focused image and the other of the areas surrounds the first area.

7. Apparatus as claimed in claim 6 in which one area has a different opacity with respect to the other area so that, if the detector means is arranged behind the two areas, the radiation received by the detector means varies as the focused image is moved from one area to the other by a fault or flaw in the object under test.

8. Apparatus as claimed in claim 7 in which one area has a transmission characteristic whereby it transmits or reflects half the intensity of the focused image striking it, the other area transmitting or reflecting substantially all of the focused image striking it.

9. Apparatus as claimed in claim 8 in which said areas are defined by optical fibres.

10. Inspection apparatus for inspecting an object transparent to radiation, comprising:
    a laser for producing radiation along a first optical path;
    first lens means in the first optical path for focusing the radiation from the laser and thereby forming a narrow beam;
    a beam splitter means on said first optical path, said beam splitter means comprising a mirror on a first surface thereof and having a central aperture through which the beam from the laser passes and emerges from said first surface;
    a mirror drum on said first optical path, said mirror drum comprising a plurality of flat mirror facets arranged so as to be rotatable about an axis, said mirror drum forming a scanner which, upon rotation about said axis, scans the beam formed by the first lens means across and through the object under inspection;

means for mounting said object under inspection on said first optical path;

a retro-reflecting sheet being arranged both as to position and extent so as to receive the beam of radiation after it has been transmitted through the object under inspection to form an image on said retro-reflecting sheet; and to reflect said image in the form of radiation along a second optical path that is substantially coincident with said first optical path;

second lens means for bringing said reflected image into focus, said second lens means receiving radiation in the form of said image along said second optical path and via said mirror drum and via the first surface of said beam splitter means, said beam splitter means causing said second optical path to depart from coincidence with said first optical path;

a target apparatus comprising a plurality of separate portions on said second optical path and adapted to receive the reflection from said beam splitter means;

the target apparatus and the retro-reflecting sheet being at conjugate points with respect to the second lens means;

separate detector means connected to each of said portions of said target apparatus, said separate detector means being arranged in conjunction with each other so as to be sensitive to changes in the position in any direction of the focused image, to the size of said focused image, and to the intensity of said focused image.

11. Inspection apparatus as claimed in claim 10 in which said first and second lens means each comprises multiple element lenses.

* * * * *